United States Patent
Kliche et al.

(10) Patent No.: US 9,144,563 B2
(45) Date of Patent: *Sep. 29, 2015

(54) TREATMENT OF TRIPLE RECEPTOR NEGATIVE BREAST CANCER

(75) Inventors: Kay-Oliver Kliche, Grafelfing (DE); Axel Mescheder, Worthsee (DE); Martine Piccart, Brussels (BE)

(73) Assignee: Medigene AG, Planegg/Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/430,393

(22) Filed: Mar. 26, 2012

(65) Prior Publication Data

US 2012/0183604 A1 Jul. 19, 2012

Related U.S. Application Data

(63) Continuation of application No. 12/293,039, filed as application No. PCT/EP2007/002352 on Mar. 16, 2007, now Pat. No. 8,168,216.

(30) Foreign Application Priority Data

Mar. 22, 2006 (EP) .................................. 06005893

(51) Int. Cl.
A61K 9/127 (2006.01)
A61K 31/337 (2006.01)
A61K 45/06 (2006.01)

(52) U.S. Cl.
CPC .............. A61K 31/337 (2013.01); A61K 9/127 (2013.01); A61K 45/06 (2013.01)

(58) Field of Classification Search
USPC ........................................................ 424/450
See application file for complete search history.

(56) References Cited

U.S. PATENT DOCUMENTS

| | | | |
|---|---|---|---|
| 5,415,869 A | 5/1995 | Straubinger et al. | |
| 5,834,012 A | 11/1998 | Perez-Soler et al. | |
| 6,214,821 B1 | 4/2001 | Daoud | |
| 6,627,614 B1 | 9/2003 | Rubinfeld | |
| 2003/0137067 A1* | 7/2003 | Cooper et al. | 264/5 |
| 2005/0202076 A1* | 9/2005 | Mundus et al. | 424/450 |
| 2005/0271714 A1* | 12/2005 | McDonald et al. | 424/450 |
| 2008/0063714 A1* | 3/2008 | Sahouani et al. | 424/484 |
| 2009/0317456 A1 | 12/2009 | Karrasch et al. | |

FOREIGN PATENT DOCUMENTS

| | | |
|---|---|---|
| CA | 2601067 | 11/2006 |
| WO | 93/18751 | 9/1993 |
| WO | 01/82899 | 11/2001 |
| WO | 2005/039533 | 5/2005 |
| WO | 2006/117220 | 11/2006 |

OTHER PUBLICATIONS

Mathias et al.: "EndoTAG-1 for treatment of triple negative breast cancer: Phase II trial results", Jun. 24, 2010.
(Continued)

Primary Examiner — Gollamudi Kishore
(74) Attorney, Agent, or Firm — Lee & Hayes, PLLC

(57) ABSTRACT

The present invention relates to the use of a liposomal preparation for the manufacture of a pharmaceutical composition and the use of such a composition for the treatment of "triple receptor negative" breast cancer.

23 Claims, 1 Drawing Sheet

(56) References Cited

OTHER PUBLICATIONS

Chebil et al.: "Comparison of Immunohistochemical and Biochemical Assay of Steroid Receptors in Primary Breast Cancer", Acta Oncologica, vol. 42, No. 7, 2003, pp. 719-725.

Yamashita et al.: "Immunohistochemical evaluation of hormone receptor status for predicting response to endocrine therapy in metastatic breast cancer", Breast Cancer, vol. 13, 2006, pp. 74-83.

Kallioniemi et al.: "ERBB2 amplification in breast cancer analyzed by fluorescence in situ hybridization", PNAS, vol. 89, 1992, pp. 5321-5325.

Awada et al.: "Final results of a controlled, randomized 3-arm phase II trial of EndoTAG-1, a cationic liposomal formulation of paclitaxel targeting tumor endothelial cells, in advanced triple-negative breast cancer (TNBC)", San Antonio Breast Cancer Symposium, Dec. 9, 2011.

Trosko in Mutation Research, 480-481, pp. 219-229 (2001).

Dent et al., "Triple-Negative Breast Cancer: Clinical Features and Patterns of Recurrence", Clinical Cancer Research, 2007, vol. 13, pp. 4429-4434.

Carey et al., "The Triple Negative Paradox: Primary Tumor Chemosensitivity of Breast Cancer Subtypes", 2007, vol. 13, pp. 2329-2334.

Sotiriou et al., "Breast cancer classification and prognosis based on gene expression profiles from a population-based study", Proceedings of the National Academy of Sciences, 2003, vol. 13, pp. 10393-10398.

Ignatiadis et al., "Feasibility study of cationic liposome-encapsulated paclitaxel in combination with paclitaxel followed by FEC as induction therapy in HER2-negative breast cancer", J. Clin. Oncol. (2013 ASCO Annual Meeting), 2013, vol. 31, Abstract Only.

Medigene AG Press Release, "Medigene publishes final results from phase II Investigator Initiated Trial of EndoTAG®-1 at ASCO 2013" May 16, 2013.

* cited by examiner

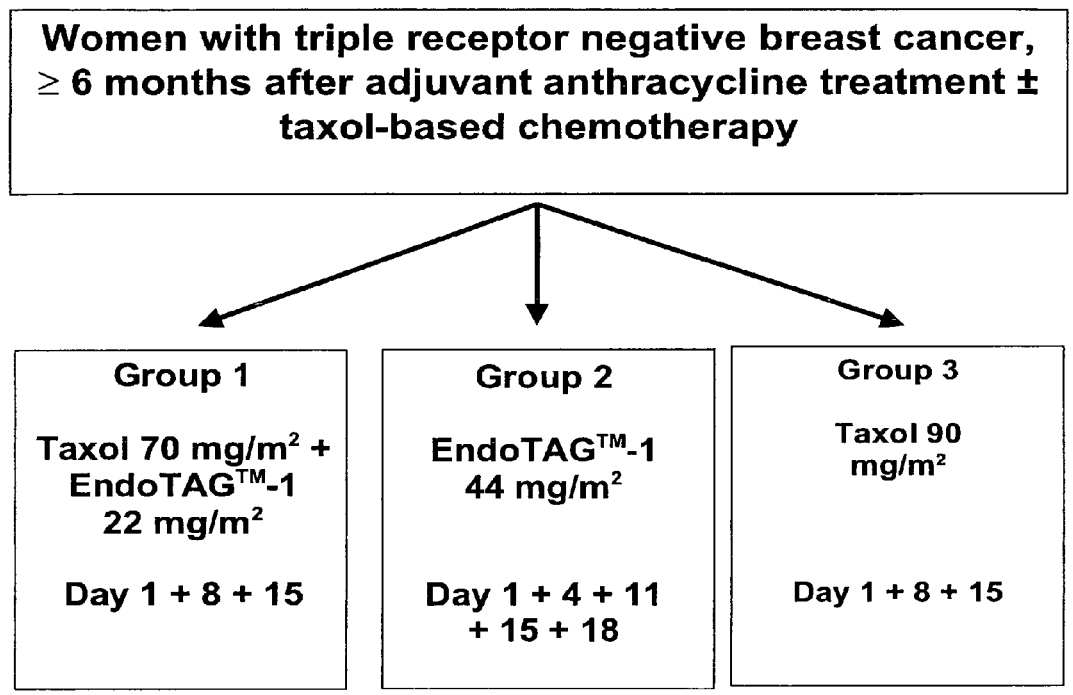

TREATMENT OF TRIPLE RECEPTOR NEGATIVE BREAST CANCER

RELATED APPLICATIONS

This application is a Continuation of U.S. patent application Ser. No. 12/293,039, filed on Jan. 9, 2009, which is a U.S. National Phase Application of International Application No. PCT/EP2007/002352, filed Mar. 16, 2007, which claims the benefit of European Patent Application No. 06005893.0 filed Mar. 22, 2006, both of which are herein incorporated by reference in their entirety.

BACKGROUND

The present invention relates to the use of a liposomal preparation for the manufacture of a pharmaceutical composition and the use of such a composition for the treatment of "triple receptor negative" breast cancer.

Today the systemic treatment of breast cancer offers three major different treatment modalities and the applicability of these different treatment options is substantially dependent on the receptor status of the patient (Bernard-Marty et al., 2004). Endocrine and biological therapy requires the presence of the respective receptors on the cancer cells, whereas cytotoxic chemotherapy is independent of those specified receptors.

In patients with hormone-receptor-positive breast cancer, endocrine therapy or a combination thereof is usually the treatment of choice (Bernard-Marty et al., 2004; Gradishar, 2004). In the presence of estrogen receptor (ER) and/or progesterone receptor (PgR) response rates of greater than 80% have been observed. In general, postmenopausal patients exhibit higher ER and PgR expression than their premenopausal counterparts.

The gold standard in endocrine therapy has been the selective ER modulator tamoxifen. It inhibits binding of estrogen to the estrogen receptor, thereby disrupting a series of cellular mechanisms that regulate cellular replication. Despite being tolerated well in most cases, tamoxifen is associated to a number of adverse events. Although the drug has a high overall response rate, disease relapse and resistance develop in many patients. The resistance might be related to an altered interaction between tamoxifen and the estrogen receptor.

To overcome resistance, alternative endocrine therapies have been developed that challenge the role of tamoxifen (Bernard-Marty et al., 2004) (Gradishar, 2004). Aromatase inhibitors directly interfere with the biosynthesis of estrogen by inhibiting the enzyme aromatase which converts androstenedione into estradiol. The latest generation of these inhibitors comprises nonsteroidal drugs like letrozol, anastrozol and vostrozol and steroidal drugs like exemestane. The favourable safety and response rates for this class of medicaments has established aromatase inhibitors as the standard endocrine therapy for the treatment of metastatic breast cancer in postmenopasal women.

The antiestrogen fulvestrant circumvents resistance issues related to tamoxifen by a different mechanism of action. It binds the ER, thereby inhibiting DNA binding and decreases the ER concentration by promoting the degradation of the ER.

In pre-menopausal ER and PgR positive women, endocrine therapies beside tamoxifen include ovarian ablation by surgery or radiotherapy and luteinizing hormone releasing hormone (LHRH) analogues (Bernard-Marty et al., 2004). In these patients, the ovaries are the major source of estrogen synthesis and ovarian ablation was the original therapy for breast cancer. To avoid the adverse events of ovaraian ablation by surgery or irradiation, the ovarian function can be suppressed by LHRH analogues. LHRH analogue like goserelin, leuprolide and triptorelin suppress the ovarian estrogen production by down regulation of pituitary release of gonadotropins through their antagonistic action on the GnRH (gonadotropins-releasing hormone) receptors (Prowell and Davidson, 2004).

With growing understanding and intense research in the biology of breast cancer, several new defined targets for antitumour therapy have emerged in the last years. Among those, HER-2/neu has been established as a main target for therapy. The human endothelial growth factor receptor 2 (HER-2) is amplified and/or overexpressed in approximately 30% of breast cancer tumours (Slamon et al., 1987) and is targeted by the inhibitory antibody trastuzumab. As trastuzumab is one of the few agents that led to an improvement in the overall survival in metastatic breast cancer, HER-2 status evaluation became indispensable for optimal treatment (Bernard-Marty et al., 2004).

Trastuzumab is approved for the second line treatment of metastatic breast cancer for HER-2 positive patients who have received one or more regimes of chemotherapy or for the first line treatment in combination with paclitaxel. Trastuzumab is commonly used until disease progression. It is generally well tolerated with congestive heart failure being the most important side effect. The use of trastuzumab is constantly evaluated in different mono and combination therapies with differing patient populations and dosing schedules.

The receptor status for ER, PgR and HER-2 can be determined by standard immunohistochemical or enzyme based assays (IHC) assays (Chebil et al., 2003; Yamashita et al., 2006) (Schaller et al., 2001). HER-2 status can also be assessed by the detection of gene amplification by fluorescence in situ hybridization (FISH) (Kallioniemi et al., 1992).

Overall, therapies depending on the receptor status of the patient have proven great benefit for the treatment of breast cancer.

Unfortunately about 15% of all breast cancer cases are negative for ER, PgR and HER-2. In these cases prognosis is very poor with an 80% relapse rate and a median survival of only 6 months.

For ER, PgR and HER-2 negative patients, as well as for patients with endocrine therapy resistant disease, chemotherapy is the only therapeutic option. Frequently applied chemotherapeutic drugs in breast cancer are drugs from the anthracycline class, the taxane class and to a lower extent antimetabolites, e.g. capecitabine, gemcitabine, alkylating agents and vinca alkaloids. These drugs are used in two basic applications schemes. The drugs can be applied as single agents in a sequential fashion or they can be used in a combination regime. Of course the two treatment modalities can be combined to some extent.

The anthracyclines, and especially doxorubicine and epirubicine, have been shown to be active agents in the treatment of breast cancer and anthracycline-containing combination regimes are common first line treatments in patients who have not received anthracyclines in an adjuvant setting. Common combination treatment consists for example of doxorubicine/epirubicine plus cyclophospamide, doxorubicin/epirubicin plus cyclophosphamide and 5-fluorouracil, or combinations of anthracyclines and capecitabine or gemcitabine (O'Shaughnessy, 2005).

With the common use of anthracyclines in early stages of breast cancer treatment, the likelihood of anthracycline resistant forms of breast cancer, however, increases (Bernard-Marty et al., 2004).

The introduction of the taxanes paclitaxel and docetaxel into the treatment further improved the management of the disease in first and second line treatment. Paclitaxel has a unique mechanism of action and a broad spectrum of antiproliferative activity because paclitaxel binds to microtubules, promotes tubulin polymerisation and stabilizes the assembled microtubules. As a result, paclitaxel blocks the cell cycle at prophase resulting in an accumulation of cells in the G2/M phase.

Unfortunately, paclitaxel has extreme low solubility in water, which makes it difficult to provide a suitable dosage form. Currently, paclitaxel is formulated and administered in a vehicle containing Cremophor EL (a polyethoxylated castor oil) and ethanol in a 50:50 (vol/vol) ratio. This solution is diluted 1:10 in saline before being administered to humans. However, various severe side reactions, such as hypersensitivity and hypertensive reactions, nephrotoxicity and neurotoxicity, for example, have been reported in patients due to Cremophor EL formulation.

U.S. Pat. No. 5,648,090, U.S. Pat. No. 5,424,073 and U.S. Pat. No. 6,146,659 (Rahman et al.) provide a liposomal encapsulated paclitaxel for a method for treating cancer in mammals. These patents disclose a method of administering to the host a pharmaceutical composition of a therapeutically effective amount of liposomes which include a liposome forming material, cardiolipin, and an agent such as paclitaxel, or an antineoplastic derivative of paclitaxel, or a mixture thereof, with a pharmaceutically acceptable excipient.

From U.S. Pat. No. 5,837,283 it has been known that cationic liposomes preferentially target the angiogenic endothelial cells in solid tumours. From the disclosure of WO 2005/0309533 (Teifel et al.) it is known that a treatment with paclitaxel encapsulated in cationic liposomes might proof beneficial in various cancer indications. The document discloses the application of cationic liposomal paclitaxel formulations to humans suffering from melanoma, prostate, pancreatic, gastro-intestinal, colorectal, and breast cancer. The application also describes the use of cationic liposomal paclitaxel formulations in different animal models of pancreatic cancer, uterus sarcoma, colon carcinoma and head and neck squamous-cell carcinoma.

Liposomal formulations are also known for anthraycline drugs. Doxorubicine has been encapsulated in uncharged pegylated or unpegylated liposomes for the treatment of breast cancer. These formulations have been used for the treatment of breast cancer in a first line (Chan et al., 2004) and in a second line (Keller et al., 2004) regime.

In summary most of today's therapeutical options in breast cancer are dependent on the receptor status of the patients. Particularly patients of the triple receptor negative subgroup are not eligible to the highly effective endocrine therapies. The options for chemotherapeutical treatment are limited and a resistance against the existing regimes like the anthracyclines is frequently observed. Consequently there is a high unmet medical need for the development of new therapies in this indication.

Thus, it was the underlying problem of the present invention to provide an improvement in the treatment of triple receptor negative breast cancer, especially for patients who have become refractory to anthracycline treatment.

DESCRIPTION OF THE INVENTION

The problem was solved by providing a new pharmaceutical composition for the treatment of triple receptor negative breast cancer. The composition can be applied in different schedules either as a mono- or a combination therapy.

A first aspect of the present invention relates to the use of a cationic liposomal preparation comprising at least one cationic lipid, an antimitotic agent and optionally at least one neutral and/or anionic lipid for the manufacture of a pharmaceutical composition for the treatment of triple receptor negative breast cancer in a human or animal.

In a preferred embodiment, the cationic liposomal preparation comprises at least one cationic lipid from about 30 mol % to about 99.9 mole %, an antimitotic agent in an amount of at least about 0.1 mol % and optionally at least one neutral and/or anionic lipid from about 0 mole % to about 70 mole %.

The antimitotic agent is preferably a taxane, preferably paclitaxel or a derivative thereof such as docetaxel. Further suitable antimitotic agents are anthracyclines, preferably doxorubicine or epirubicine, thalidomide, vinca alkaloids like vinebreline or vincristine, other agents interacting with microtubuli such as discodermolide, laulimalide, isolaulimalide, eleutherobin, Sarcodictyin A and B.

The cationic liposomal preparation may be used in a monotherapy or in a combination therapy, for example in combination therapy with a therapeutically effective dose of at least one further active agent, which may be administered as a preparation, which is not a cationic liposomal preparation, e.g. a non-liposomal preparation. The further active agent may be a chemotherapeutic agent such as an anthracycline, and/or a further taxane, e.g. paclitaxel.

For the treatment of triple receptor negative breast cancer, the inventors assume that the application of an antimitotic agent, e.g a taxane, formulated in cationic liposomes, has an improved ratio of clinical response to side effects over the application of a an antimitotic agent in a non-liposomal formulation. This effect could not be predicted in the prior art, since cationic liposomes target the drug to endothelial cells of a tumour which only constitute a minor part of the tumour entity.

Furthermore, the inventors assume that a combination therapy of an antimitotic agent in a liposomal formulation with a further agent, e.g. an antimitotic agent in a non-liposomal formulation has an improved ratio of clinical response to side effect compared to the application of a non-liposomal formulation alone, when applied in similar cumulated doses. This synergistic effect could not be predicted in the prior art. As mentioned afore, the different formulations target the drugs to different locations within in the tumour. It could not be predicted that drugs with the same mode of action, like antimitotic agents, exhibit a synergistic effect when acting on different cells within a tumour.

Preferred examples for the use of pharmaceutical compositions comprising paclitaxel in cationic liposomes for the treatment of various tumours in humans are disclosed in WO 2005/0309533 (Teifel et al.).

As a particular advantage, the present invention offers a new treatment for a subtype of breast cancer which had only limited treatment options due to its biological properties. It should be noted, however, that the above combination therapy is also useful in other medical indications, e.g. the treatment of hyperproliferative disorders, e.g. angiogenic and/or vascular disorders or cancer in general.

A particular advantage of the combination therapy is that the side effects of the active agents are reduced. Consequently it is very advantageous to increase the applied doses of chemotherapeutic agents by administering a combination of agents in liposomal and non-liposomal formulations without increasing the side effects. Compared to the traditional treatment of patients suffering from triple receptor negative cancer or other disorders, the combination therapy improves the efficacy of the treatment and decreases the side effects.

A further aspect of the invention refers to a combination of
  a) a cationic liposomal preparation comprising at least one cationic lipid, an antimitotic agent and optionally at least one neutral and/or anionic lipid and
  b) a non-liposomal preparation comprising an antimitotic agent, for simultaneous, separate and/or sequential administration to a human or an animal.

Still further aspect of the invention refers to a combination of:
  a) a cationic liposomal preparation as described above, which preferably comprises at least one cationic lipid from about 30 mol % to about 99.9 mole %, an antimitotic agent, e.g. a taxane in an amount of at least about 0.1 mol % and optionally at least one neutral and/or anionic lipid from about 0 mole % to about 70 mole % and
  b) a non-liposomal preparation comprising an antimitotic agent, for simultaneous, separate or sequential use to a human or an animal body. Preferred is the treatment of cancer.

Still a further aspect of the invention refers to a method of treating triple receptor negative breast cancer comprising the administration of a cationic liposomal preparation comprising at least one cationic lipid, an antimitotic agent and optionally at least one neutral and/or anionic lipid and preferably comprising at least one cationic lipid from about 30 mol % to about 99.9 mole %, an antimitotic agent, e.g. a taxane in an amount of at least about 0.1 mol % and optionally at least one neutral and/or anionic lipid from about 0 mole % to about 70 mole % in a therapeutically effective dose to a subject in need thereof.

Still a further aspect of the invention refers to a method of treating a hyperproliferative disorder comprising the administration of a combination as described above in a therapeutically effective dose to a subject in need thereof.

Especially preferred embodiments of the invention relating to cationic liposomal preparations, combinations of a cationic liposomal preparation and a non-liposomal preparation for the treatment for triple receptor negative breast cancer are described in the following specifications and examples in more detail.

"About" in the context of amount values refers to an average deviation of maximum +/−20%, preferably +/−10% based on the indicated value. For example, an amount of about 30 mol % cationic lipid refers to 30 mol %+/−6 mol % and preferably 30 mol %+/−3 mol % cationic lipid with respect to the total lipid/amphiphile molarity.

"Active agent" refers to an agent that is therapeutically effective.

"Carrier" refers to a diluent, adjuvant, excipient, or vehicle which is suitable for administering a diagnostic or therapeutic agent. The term also refers to a pharmaceutical acceptable component(s) that contains, complexes or is otherwise associated with an agent to facilitate the transport of such an agent to its intended target site. Carriers include those known in the art, such as liposomes, polymers, lipid complexes, serum albumin, antibodies, cyclodextrins and dextrans, chelate, or other supramolecular assemblies.

"Combination" or "co-administration" refers to an administration schedule that is synchronous, serial, overlapping, alternating, parallel, or any other treatment schedule in which the various agents or therapies are administered as part of a single treatment regimen, prescription or indication or in which the time periods during which the various agents or therapies that are administered otherwise partially or completely coincide.

The term "derivative" refers to a compound derived from some other compound while maintaining its general structural features. Derivatives may be obtained for example by chemical functionalization or derivatization.

The terms "liposome" and "liposomal preparation" are used synonymously throughout the present application. "Liposome" refers to a microscopic spherical membrane-enclosed vesicle (about 50-2000 nm diameter). The term "liposome" encompasses any compartment enclosed by a lipid bilayer. Liposomes are also referred to as lipid vesicles. In order to form a liposome the lipid molecules comprise elongated non polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell.

Thus, the bilayer of a liposome has similarities to a cell membrane without the protein components present in a cell membrane. As used in connection with the present invention, the term liposome includes multilamellar liposomes, which generally have a diameter in the range of about 1 to 10 micrometers and are comprised of anywhere from two to hundreds of concentric lipid bilayers alternating with layers of an aqueous phase, and also includes unilamellar vesicles which are comprised of a single lipid layer and generally have a diameter in the range of about 20 to about 400 nanometers (nm), about 50 to about 300 nm, about 300 to about 400 nm, about 100 to about 200 nm, which vesicles can be produced by subjecting multilamellar liposomes to ultrasound, by extrusion under pressure through membranes having pores of defined size, or by high pressure homogenization. Preferred liposomes would be unilamellar vesicles, which have a single lipid bilayer, and a diameter in the range of about 25-400 nm.

The term "taxane" as used herein refers to the class of antineoplastic agents having a mechanism of microtubule action and having a structure that includes the unusual taxane ring structure and a stereospecific side chain that is required for cytostatic activity. Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. The active agent paclitaxel and docetaxel both belong to the taxane class.

"Paclitaxel" (which should be understood herein to include analogues, formulations, and derivatives such as, for example, docetaxel, taxotere (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from Taxus brevifolia; or T-1912 from Taxus yannanensis). Paclitaxel should be understood to refer to not only the common chemically available form of paclitaxel, but analogs (e.g., taxotere, as noted above) and paclitaxel conjugates (e.g., paclitaxel-PEG, paclitaxeldextran, or paclitaxel-xylose).

A "therapeutically effective dose" is the dose of an active agent or a pharmaceutical composition that is sufficient to achieve the desired therapeutical result in the treated subject.

The term "zeta potential" refers to a measured electrical potential of a particle, such as a liposome, measured with an instrument such as a Zetasizer 3000 using Laser Doppler micro-electrophoresis under the conditions specified. The zeta potential describes the potential at the boundary between bulk solution and the region of hydrodynamic shear or diffuse layer. The term is synonymous with "electrokinetic potential" because it is the potential of the particles which acts outwardly and is responsible for the particle's electrokinetic behavior.

Wherever there is the unit mg/m$^2$ bs or just mg/m$^2$ usually refers to mg active agent, e.g. paclitaxel, per m$^2$ human body surface (bs).

The preferred cationic lipids of the liposomal preparation are N-[1-(2,3-dioleoyloxy)propyl]-N,N,N-trimethyl ammonium salts, e.g. the methylsulfate (DOTAP). Other useful lipids for the present invention may include: DDAB, dimethyldioctadecyl ammonium bromide; 1,2-diacyloxy-3-trimethylammonium propanes, (including but not limited to: dioleoyl, dimyristoyl, dilauroyl, dipalmitoyl and distearoyl; also two different acyl chain can be linked to the glycerol backbone); N-[1-(2,3-dioloyloxy)propyl]-N,N-dimethyl amine (DODAP); 1,2-diacyloxy-3-dimethylammonium propanes, (including but not limited to: dioleoyl, dimyristoyl, dilauroyl, dipalmitoyl and distearoyl; also two different acyl chain can be linked to the glycerol backbone); N-[1-(2,3-dioleyloxy)propyl]-N,N,N-trimethylammonium chloride (DOTMA); 1,2-dialkyloxy-3-dimethylammonium propanes, (including but not limited to: dioleyl, dimyristyl, dilauryl, dipalmityl and distearyl; also two different alkyl chain can be linked to the glycerol backbone); dioctadecylamidoglycylspermine (DOGS); 3β-[N—(N',N'-dimethylamino-ethane)carbamoyl] cholesterol (DC-Chol); 2,3-dioleoyloxy-N-(2-(sperminecarboxamido)-ethyl)-N,N-dimethyl-1-propanaminium trifluoro-acetate (DOSPA); β-alanyl cholesterol; cetyl trimethyl ammonium bromide (CTAB); diC14-amidine; N-tert-butyl-N'-tetradecyl-3-tetradecylamino-propionamidine; 14Dea2; N-(alpha-trimethylammonioacetyl)didodecyl-D-glutamate chloride (TMAG); O,O'-ditetradecanoyl-N-(trimethylammonio-acetyl)diethanolamine chloride; 1,3-dioleoyloxy-2-(6-carboxy-spermyl)-propylamide (DOSPER); N,N,N',N'-tetramethyl-N,N'-bis(2-hydroxylethyl)-2,3-dioleoyloxy-1,4-butanediammonium iodide; 1-[2-(acyloxy)ethyl]-alkyl (alkenyl)-3-(2-hydroxyethyl)-imidazolinium chloride derivatives as described by Solodin et al. (Solodin et al., 1995), such as 1-[2-(9(Z)-octadecenoyloxy)ethyl]-2-(8(Z)-heptadecenyl-3-(2-hydroxyethyl)imidazolinium chloride (DOTIM), 1-[2-(hexadecanoyloxy)ethyl]-2-pentadecyl-3-(2-hydroxyethyl)imidazolinium chloride (DPTIM), 2,3-dialkyloxypropyl quaternary ammonium compound derivatives, containing a hydroxyalkyl moiety on the quaternary amine, as described e.g. by Feigner et al. (Feigner et al., 1994) such as: 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyloxypropyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), 1,2-disteryloxypropyl-3-dimethyl-hydroxyethyl ammonium bromide (DSRIE); cationic esters of acyl carnitines as reported by Santaniello et al. [U.S. Pat. No. 5,498,633]; cationic triesters of phospahtidylcholine, i.e. 1,2-diacyl-sn-glycerol-3-ethylphosphocholines, where the hydrocarbon chains can be saturated or unsaturated and branched or non-branched with a chain length from $C_{12}$ to $C_{24}$, the two acyl chains being not necessarily identical.

In a preferred embodiment, the liposomal preparation optionally comprises at least one neutral and/or anionic lipid. Neutral lipids are lipids which have a neutral net charge. Anionic lipids or amphiphiles are molecules which have a negative net charge. These can be selected from sterols or lipids such as cholesterol, phospholipids, lysolipids, lysophospholipids, sphingolipids or pegylated lipids with a neutral or negative net change. Useful neutral and anionic lipids thereby include: phosphatidylserine, phosphatidylglycerol, phosphatidylinositol (not limited to a specific sugar), fatty acids, sterols, containing a carboxylic acid group for example, cholesterol, 1,2-diacyl-sn-glycero-3-phosphoethanolamine, including, but not limited to, DOPE, 1,2-diacylglycero-3-phosphocholines and sphingomyelin. The fatty acids linked to the glycerol backbone are not limited to a specific length or number of double bonds. Phospholipids may also have two different fatty acids. Preferably the further lipids are in the liquid crystalline state at room temperature and they are miscible (i.e. a uniform phase can be formed and no phase separation or domain formation occurs) with the used cationic lipid, in the ratio as they are applied. In a preferred embodiment the neutral lipid is DOPC.

In a further preferred embodiment, the liposomal preparation comprises optionally neutral and/or anionic lipids, preferably DOPC in an amount of about 30 mole % to about 70 mole %, preferably from about 40 mole % to about 60 mole % and more preferably from about 45 mole % to about 55 mole %.

It is a further object of the present invention that the cationic liposome preparation which is used therein can be dehydrated, stored for extended periods of time while dehydrated, and then rehydrated when and where it is to be used, without losing a substantial portion of its contents during the dehydration, storage and rehydration processes. To achieve the latter, one or more protective agents, such as cryoprotectants, may be present. Thus, the inventive cationic liposome preparation preferably comprises a cryoprotectant, wherein the cryoprotectant is selected from sugars or alcohols or combinations thereof. Preferably, the cryoprotectant is selected from trehalose, maltose, sucrose, glucose, lactose, dextran, mannitol, sorbitol or combinations thereof. In a preferred embodiment, the liposomal preparation comprises trehalose in the range of about 5% (m/v) to about 15% (m/v) with respect to the total volume of the preparation.

In a preferred embodiment of the present invention, the taxane is paclitaxel or a derivative thereof. The cationic liposomal preparation may comprise paclitaxel in an amount of at least about 2 mole % to about 8 mole %, preferably from at least 2.5 mole % to about 3.5 mole %.

In a specially preferred embodiment the cationic liposomal preparation DOTAP, DOPC and paclitaxel in a ratio of about 50:47:3. This formulation is also designated MBT-0206 or EndoTAG-1. EndoTAG-1 has a lipid content of 10 mM in a 10% m/m trehalose dihydrate solution. The manufacture of such a formulation is disclosed in WO 2004/002468, which is herein incorporated by reference.

Preferably, the liposomal preparation has a zeta potential in the range of about 0 mV to about 100 mV, preferably in the range of about 20 mV to about 100 mV in about 0.05 mM KCl solution at about pH 7.5.

The described liposomes are used for the manufacture of a pharmaceutical composition for the treatment of breast cancer which is can not be treated by endocrine therapy and HER-2 related therapy. Preferably triple receptor negative breast cancer is treated. The indication triple receptor negative breast cancer comprises breast cancer with a negative receptor status for the estrogen receptor (ER) progesterone receptor (PgR) and HER-2 receptor (Her-2). Determination of the receptor status is an established diagnostic procedure for breast cancer and known in the field of art. ER, PgR and HER-2 status can be determined by standard immunohistochemical or enzyme based assays (IHC) assays (Chebil et al., 2003; Yamashita et al., 2006) (Schaller et al., 2001). HER-2 status can also be assessed by the detection of gene amplification by fluorescence in situ hybridization (FISH) (Kallioniemi et al., 1992).

The pharmaceutical composition can be used in a first-, second-, or third line treatment. Patients who are treated may have undergone surgery for tumour resection, radiotherapy and/or chemotherapy. A frequent chemotherapy for breast cancer are anthracycline-based combination regimes. Typically this combination regimens comprise an anthracycline drug, e.g. doxorubicine or epirubicine. The first line treatment might involve a combination therapy of an anthracycline drug and a taxane drug. The patients may be pre- or post-menopausal. The cancer to be treated can be in different clinical stages according to size, distribution and degree metastasis formation.

The pharmaceutical composition may be administered to the patient at a therapeutically effective dose at least once a week but it may also be administered several times a week. In a preferred embodiment the pharmaceutical composition is administered once or twice a week. The composition may also be administered in varying times per week during the treatment period.

The application of the composition may be omitted for at least one week during the treatment schedule. Depending on the duration of the treatment and on the observed side effects, the application may also be omitted for several times during a treatment period.

Preferably, the liposomal preparation is administered in single doses from about 1 mg/m$^2$ to about 50 mg/m$^2$ per administration. In a preferred embodiment the preparation is administered at a dose between about 20 mg/m$^2$ and about 50 mg/m$^2$ per administration. In an especially preferred embodiment the preparation is administered at a dose of about 22 mg/m$^2$ or about 44 mg/m$^2$ per administration. In another especially preferred embodiment of the invention, the preparation is administered twice a week in a dose of about 44 mg/m$^2$. In a most preferred embodiment of the invention, the liposomal preparation is administered on days 1, 5, 8, 11, 15, 18, 22, 25, 29, 32, 36 and 39 of the treatment cycle followed by a 14-day treatment free interval or on days 1, 4, 8, 11, 15 and 18 of the treatment cycle followed by a 10-day treatment-free interval. The treatment cycles may be repeated several times if desired, e.g. at least 2, 3 or 4 times.

It is another important aspect of the present invention, that the cationic liposomal formulation can be used in a simultaneous, separate, or sequential combination therapy. The combination therapy additionally involves the administration of a therapeutically effective dose of at least one further active agent. In one embodiment the further active agent is in a non-liposomal formulation. The combination therapy may involve simultaneous, separate and/or sequential administration to a human or to an animal. In the simultaneous combination therapy the liposomal preparation and the further active agent are administered on the same day.

The liposomal preparation and the further active agent may be administered on different timepoints on the same day or on different days. In a preferred embodiment the liposomal preparation is administered prior to the further active agent, preferably more than one hour, but not more then twelve hours prior to the application of the further active agent.

The further active agent may be selected from cytotoxic or cytostatic substances such as an anti-tumour or an anti-endothelial cell active substance, a chemotherapeutic agent or an immunological active substance, a compound that reduces or eliminates hypersensitivity reactions or a chemosensitizer or combinations thereof.

In a preferred embodiment, the further active agent is selected from an antineoplastic agent, especially an antimitotic agent like a taxane, an anthracycline preferably doxorubicine or epirubicine, a statin, a depsipeptide, thalidomide, other agents interacting with microtubuli such as discodermolide, laulimalide, isolaulimalide, eleutherobin, Sarcodictyin A and B, alkylating agents especially platinum containing compounds like cisplatin, carboplatin, DNA topoisomerase inhibiting agents like camptothecin, RNA/DNA antimetabolites, especially 5-fluorouracil, gemcitabine or capecitabine. In a most preferred embodiment, it is selected from paclitaxel, docetaxel, camptothecin or any derivative thereof.

The compound that reduces or eliminates hypersensitivity reactions may be selected from the group comprising steroids, antihistamines, H2 receptor antagonists, and combinations thereof in a sufficient amount to prevent fatal anaphylactic reactions. Said compound can also be selected from the group comprising Ranitidine, Dexamethasone, Diphenhydramine, Famotidine, Hydrocortisone, Clemastine, Cimetidine, Prednisolone, Chlorpheniramine, Chlorphenamine, Dimethindene maleate, and Promethazine.

The chemosensitzier may be selected from the group comprising cell cycle modulators, substances that revert a drug resistance like verapamil, vasoactive substances like antihypertensive drugs, and substances that modify interactions of cationic liposomes with blood components like protamine.

It is a preferred embodiment of the invention-to use a liposomal preparation in a combination therapy together with a non-liposomal taxane such as paclitaxel or a derivative thereof. Preferably the paclitaxel is formulated in Cremophore EL or as a Albumin conjugate. In a most preferred embodiment a liposomal preparation comprising DOTAP, DOPC and paclitaxel, is used in a combination therapy together with a non-liposomal taxane, e.g. paclitaxel or a derivative thereof.

It is an aspect of the present invention that in the combination therapy, the non-liposomal taxane may be applied in a lower weekly dose compared to the standard monotherapy. In a preferred embodiment the liposomal preparation is administered at a weekly dose between about 20 mg/m$^2$ and 50 mg/m$^2$ and the non-liposomal taxane formulation is administered at a weekly dose between 25 mg/m$^2$ and 100 mg/m$^2$.

In a preferred embodiment the liposomal preparation and the non-liposomal taxane are administered once a week.

In current treatment schedules, 80 to 150 mg/m$^2$ non-liposomal paclitaxel is administered once weekly. Docetaxel is administered at 35 to 40 mg/m$^2$ or about 70 mg/m$^2$ in the once weekly regime (Eniu et al., 2005).

In a preferred embodiment of the invention the liposomal preparation is administered once weekly in combination with about 60 mg/m² non-liposomal paclitaxel. In another preferred embodiment of the invention the liposomal preparation is administered once weekly in combination with about 25-35 mg/m² non-liposomal docetaxel.

In a most preferred embodiment the liposomal preparation is administered once a week at a dose of about 22 mg/m² and non-liposomal paclitaxel or a derivative is administered once a week at a dose of about 60 mg/m² or about 70 mg/m² preferably on the same day.

In a most preferred embodiment composition is applied together with the non-liposomal formulation on days 1, 8, 15, 22, 29, 36 of a treatment cycle followed by a 14-day treatment free interval, or on days 1, 8, 15 of a treatment cycle followed by a 13-day treatment-free interval. The treatment cycles may be repeated several times if desired, e.g. at least 2, 3 or 4 times.

The liposomal preparation may be administered systemically, preferably intravenously. The liposomal preparation may be administered together with physiologically acceptable carriers such as a buffer.

Usually, the pharmaceutical composition will be supplied in a dehydrated form. Prior to application, the composition will be hydrated in pharmaceutical grade water or saline or another suitable liquid, preferably comprising physiologically acceptable carriers such as a buffer.

FIGURE LEGENDS

FIG. 1

Clinical trial of EndoTAG®-1 in triple receptor negative breast cancer.

Schematic diagram of a dose schedule comparing the administration of Taxol® with the administration of EndoTAG®-1 alone or in combination with Taxol® in women suffering from triple receptor negative breast cancer and who received adjuvant anthracycline treatment at least until 6 months before. Group 1: Taxol® (70 mg/m²) in combination with EndoTAG®-1 (22 mg/m² liposomal paclitaxel) is administered on days 1, 8, 15 of each cycle. Group 2: EndoTAG®-1 (44 mg/m² liposomal paclitaxel) is administered on days 1, 4, 8, 11, 15, 18 of each cycle. Group 3: Taxol® (90 mg/m²) is administered on days 1, 8, 15 of each cycle (control group).

EXAMPLES

Example 1

General Human Therapy Treatment Protocol

This example is concerned with protocols for treating triple receptor negative breast cancer in human patients.

The cationic liposomal preparation can be administered as a monotherapy or in combination with a further active agent. The active agent of the liposomal preparation and the further active agent may be the same or different. The agents are selected according to several factors. These factors relate to the exact pathological state of the patient, the pre-treatment the patient has received, drug refractoryness or side effects of either active agent.

The various elements of conducting a clinical trial, including patient treatment and monitoring, will be known to those skilled in the art in light of the present disclosure.

Patients chosen for a clinical trial have objectively measurable disease as determined by physical examination, laboratory techniques, or radiographic procedures. Such patients preferably also have no history of clinically relevant cardiac or renal disease and any chemotherapy should be stopped at least 2 weeks before entry into the study.

The disclosed formulations may be administered over a short to medium infusion time. The infusion given at any dose level should be dependent upon the toxicity achieved after each infusion. Thus, if Grade II toxicity was reached after any single infusion, or at a particular period of time for a steady rate infusion, further doses should be withheld or the steady rate infusion stopped unless toxicity improved. Increasing doses should be administered to groups of patients until approximately 60% of patients showed unacceptable Grade III or IV toxicity in any category. Doses that are ⅔ of this value would be defined as the safe dose.

Physical examination, tumour measurements and laboratory tests should, of course, be performed before treatment and at intervals of about 3-4 weeks later. Laboratory tests should include complete blood cell counts, serum creatinine, creatine kinase, electrolytes, urea, nitrogen, SGOT, bilirubin, albumin and total serum protein.

Clinical responses may be defined by acceptable measure or changes in laboratory values e.g. tumor markers. For example, a complete response may be defined by the disappearance of all measurable disease for at least a month, whereas a partial response may be defined by a 50% or greater reduction.

Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA Office of Biologics standards.

Prior to application, the formulation can be reconstituted in an aqueous solution in the event that the formulation was freeze dried. As outlined above, the required application volume is calculated from the patient's body weight and the dose schedule. The route of administration preferably comprises peritoneal or parenteral administration. Typically administration will be via the intravenous route.

For use with the present invention the "therapeutically effective dose" of a composition or active agent administered to a subject will vary depending on a wide range of factors. The amount will depend upon the size, age, sex, weight, and condition of the patient, as well as the potency of the substance being administered. Having indicated that there is considerable variability in terms of dosing, it is believed that those skilled in the art can, using the present disclosure, readily determine appropriate dosing by first administering extremely small amounts and incrementally increasing the dose until the desired results are obtained.

Example 2

Phase-II Trial Evaluating the Efficacy of EndoTAG□-1 in Triple Receptor Negative Breast Cancer Patients 2.1. Study Rationale Women who have breast cancer that is "triple negative" for estrogen (ER), progesterone (PR) and HER2/neu (HER2) receptors currently have a paucity of treatment options. The "triple negative" status is associated with a poor prognosis in early breast cancer patients. The term "triple negative" is currently used as a clinical surrogate for the "basal-like" breast cancer: 80% of triple negative breast cancers are "basal-like". The "basal-like" breast cancers are a distinctive subtype of breast cancers defined by gene expression profiling (Brenton et al., 2005) (Sotiriou et al., 2003) (Sorlie et al., 2001).

2.2. Study Design

A total of 135 patients with triple negative breast cancer and meeting all study eligibility criteria are randomized to one of the following two treatment groups:

Group 1: Taxol® (70 mg/m$^2$) in combination with EndoTAG®-1 (22 mg/m$^2$ liposomal paclitaxel) on days 1, 8, 15 of each cycle followed by a 13-day treatment free interval Group 2: EndoTAG®-1 (44 mg/m$^2$ liposomal paclitaxel) monotherapy on days 1, 4, 8, 11, 15, 18 of each cycle followed by a 10-day treatment free interval Group 3: Taxol® (90 mg/m$^2$) monotherapy on days 1, 8, 15 of each cycle followed by a 13-day treatment free interval (control group).

Randomization is performed to achieve a ratio of 2:2:1 between treatment groups and stratified for adjuvant treatment with anthracycline alone or with anthracycline+Taxol®.

Each treatment cycle comprises 3 weeks of treatment followed by 1 week of rest, i.e. a total of 4 weeks.

Patients will first be treated for a minimum of 4 cycles. After an assessment of tumor response and savety responders i.e. CR, PR and SD) have the option to continue treatment, until PD or unacceptable toxicity occur.

All patients are treated until progression of disease or toxicity and followed up for survival.

2.3. Objectives

Primary objective: To assess the efficacy of EndoTAG®-1+Taxol® (combination therapy) and EndoTAG®-1 (monotherapy) as a rescue therapy for patients with anthracycline +/−Taxol® refractory triple receptor negative breast cancer.

Secondary objective: To assess the safety and tolerability of EndoTAG®-1+Taxol® (combination therapy) and EndoTAG®-1 (monotherapy) in this patient population.

2.4. Endpoints

Primary Efficacy Endpoint:

4-month progression free survival (PFS) rate calculated by the rate of randomized patients who show no progression of disease and are alive 16 weeks after first infusion of study drug.

Secondary Efficacy Endpoints:

Median PFS time

Tumor Response (CR/PR/SD/PD) at weeks 8, 16 and 24 assessed by the following variables:

Number of treatment responders, i.e. objective response (OR=Complete Response (CR)+Partial Response (PR))

Number of patients with stable disease (SD)

Median duration of objective response and stable disease 4-month-survival-rate calculated by the rate of randomized patients alive 16 weeks after first infusion of study drug Median overall survival time (OS)

Pain assessment (VAS)

Mean average change per week from baseline to end of treatment with study medication Percent of patients with improvement of at least 10 mm from baseline during treatment with study medication Percent of patients with deterioration of at least 10 mm from baseline during treatment with study medication Clinical Benefit Assessment via Quality of Life (QoL) Scale (EORTC-QoL-C30-Questionnaire)

Mean average change per week from baseline to end of treatment with study medication Percent of patients with improvement of at least 10 points from baseline during treatment with study medication Percent of patients with deterioration of at least 10 points from baseline during treatment with study medication Safety Endpoints:

Adverse Events: Incidence of and percentage of patients with treatment emergent AEs Laboratory Values: Number of clinically significant abnormal laboratory values Dose variation: Percentage of patients having high dose reductions, delays or discontinuation of study medication 2.5. Number of Subjects/Patients 135 women suffering from locally relapsed and/or metastatic, previously treated with anthracycline +/−Taxol® chemotherapy, triple receptor negative breast cancer are randomized at a ratio of 2:2:1 (54 patients with EndoTAG®-1+Taxol® combination therapy, 54 patients with EndoTAG®-1 monotherapy and 27 patients with Taxol® monotherapy).

2.6. Inclusion Criteria

1. Histologically proven triple-receptor-negative breast cancer with tumor biopsy
2. Estrogene (ER), progesterone (PR) and HER2 negative hormone status
3. Age≥18 years old
4. Tumor lesions according to RCIST criteria.
5. No lactating or pregnant patients
6. ECOG performance status 0-2
7. Minimum of 6 months after antecedent systemic anthracycline chemotherapy in adjuvant setting alone or in combination with chemo therapy.
8. Normal cardiac function (assessment of LVEF by MUGA scan or echocardiography above the lower limit of normal for the institution)
9. Adequate organ function (as defined by Neutrophils≥1.5×10$^9$/L, Platelets≥100×10$^9$/L, Hemoglobin≥10 g/dL, Total bilirubin≤1.5 UNL, ASAT (SGOT) and ALAT (SGPT)≤2.5 UNL, Alkaline phosphatase≤2.5 UNL, Creatinine≥150 μmol/L (1.5 mg/dL)
10. No other serious illness or medical condition as follow: a) Congestive heart failure or unstable angina pectoris, previous history of myocardial infarction within 1 year from study entry, uncontrolled hypertension or high-risk uncontrolled arrhythmias; b) History of active or significant neurological disorder and/or psychiatric disorder that would prohibit the understanding and giving of informed consent, and also would interfere in the clinical and radiological evaluation of central nervous system during the trial; c) Active uncontrolled infection; d) Active peptic ulcer, unstable diabetes mellitus.
11. No past or current history of other neoplasm except for curatively treated: a) Basal cell skin cancer. b) In situ carcinoma of the cervix.
12. No concurrent treatment with other experimental drugs. Participation in another clinical trial with any investigational not marketed drug within 30 days prior to study entry.
12. Written informed consent.

2.7. Drug Administration

EndoTAG®-1 and Taxol® will be administered intravenously.

EndoTAG®-1 will be administered with initially 0.5 ml/min. After 15 min administration speed will be increased to 1.0 ml/min and after further 15 min administration speed will be set to 1.5 ml/min.

2.8. Primary Efficacy Endpoint:

The PFS rate at week 16 in the EndoTAG®-1+Taxol® combination treatment arm is the primary endpoint.

The hypothesis of $H_0$: p≤30% versus $H_1$: p≥50% is tested in the combination treatment arm using a single stage design at a significance level of α=0.05.

If the true tumor response rate is 50% in the Taxol®+EndoTAG®-1 therapy the test will have a power of 1−β=0.90.

The same hypothesis will be tested for the EndoTAG®-1 monotherapy.

Example 3

Application of EndoTAG-1 in Combination with Taxotere®

3.1. Treatment Rationale

Women suffering from "triple receptor negative", locally relapsed and/or metastatic breast cancer, previously treated with anthracycline +/−Taxotere® chemotherapy are treated with a weekly combination therapy of EndoTAG-1 in combination with Taxotere®. Taxotere® comprises the drug docetaxel as active pharmaceutical ingredient.

3.2. Minimum Eligibility Criteria

Histologically proven breast cancer with tumor biopsy

Estrogen (ER), progesterone (PR) and HER2 negative hormone status, as shown by IHC, enzyme assay or FISH No lactating or pregnant patients ECOG performance status 0-1

Minimum of 6 months after antecedent systemic anthracycline chemotherapy in adjuvant setting Normal cardiac function (assessment of LVEF by MUGA scan or echocardiography above the lower limit of normal for the institution)

Adequate organ function (as defined by Neutrophils 1.5× $10^9$/L, Platelets 100×$10^9$/L, Hemoglobin 10 g/dL, Total bilirubin 1.5 UNL, ASAT (SGOT) and ALAT (SGPT) 2.5 UNL, Alkaline phosphatase 2.5 UNL, Creatinine 150 μmol/L (1.5 mg/dL)

3.3. Treatment Schedule

EndoTAG®-1 is administered in a dose of 22 mg/m² liposomal paclitaxel on days 1, 8, 15, 22, 29, 36 of each cycle followed by a 14-day treatment free interval.

Taxotere® is administered in a dose of 30 mg/m² docetaxel on days 1, 8, 15, 22, 29, 36 of each cycle followed by a 14-day treatment free interval.

both drugs are administered intravenously patients are treated until progression of disease or toxicity.

All of the compositions and methods disclosed and claimed herein can be made and carried out without undue experimentation in light of the present disclosure. While the compositions and methods of this invention have been described in terms of preferred embodiments, it will be apparent to those skilled in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Bernard-Marty, C., Cardoso, F., and Piccart, M. J. (2004). Facts and controversies in systemic treatment of metastatic breast cancer. Oncologist 9, 617-632.

Brenton, J. D., Carey, L. A., Ahmed, A. A., and Caldas, C. (2005). Molecular classification and molecular forecasting of breast cancer: ready for clinical application? J Clin Oncol 23, 7350-7360.

Chan, S., Davidson, N., Juozaityte, E., Erdkamp, F., Pluzanska, A., Azarnia, N., and Lee, L. W. (2004). Phase III trial of liposomal doxorubicin and cyclophosphamide compared with epirubicin and cyclophosphamide as first-line therapy for metastatic breast cancer. Ann Oncol 15, 1527-1534.

Chebil, G., Bendahl, P. O., Idvall, I., and Ferno, M. (2003). Comparison of immunohistochemical and biochemical assay of steroid receptors in primary breast cancer—clinical associations and reasons for discrepancies. Acta Oncol 42, 719-725.

Eniu, A., Palmieri, F. M., and Perez, E. A. (2005). Weekly administration of docetaxel and paclitaxel in metastatic. or advanced breast cancer. Oncologist 10, 665-685.

Feigner, J. H., Kumar, R., Sridhar, C. N., Wheeler, C. J., Tsai, Y. J., Border, R., Ramsey, P., Martin, M., and Feigner, P. L. (1994). Enhanced gene delivery and mechanism studies with a novel series of cationic lipid formulations. J Biol Chem 269, 2550-2561.

Gradishar, W. J. (2004). Tamoxifen—what next? Oncologist 9, 378-384.

Kallioniemi, O. P., Kallioniemi, A., Kurisu, W., Thor, A., Chen, L. C., Smith, H. S., Waldman, F. M., Pinkel, D., and Gray, J. W. (1992). ERBB2 amplification in breast cancer analyzed by fluorescence in situ hybridization. Proc Natl Acad Sci USA 89, 5321-5325.

Keller, A. M., Mennel, R. G., Georgoulias, V. A., Nabholtz, J. M., Erazo, A., Lluch, A., Vogel, C. L., Kaufmann, M., von Minckwitz, G., Henderson, I. C., et al. (2004). Randomized phase III trial of pegylated liposomal doxorubicin versus vinorelbine or mitomycin C plus vinblastine in women with taxane-refractory advanced breast cancer. J Clin Oncol 22, 3893-3901.

O'Shaughnessy, J. (2005). Extending survival with chemotherapy in metastatic breast cancer. Oncologist 10 Suppl 3, 20-29.

Prowell, T. M., and Davidson, N. E. (2004). What is the role of ovarian ablation in the management of primary and metastatic breast cancer today? Oncologist 9, 507-517.

Schaller, G., Evers, K., Papadopoulos, S., Ebert, A., and Buhler, H. (2001). Current use of HER2 tests. Ann Oncol 12 Suppl 1, S97-100.

Slamon, D. J., Clark, G. M., Wong, S. G., Levin, W. J., Ullrich, A., and McGuire, W. L. (1987). Human breast cancer: correlation of relapse and survival with amplification of the HER-2/neu oncogene. Science 235, 177-182.

Solodin, I., Brown, C. S., Bruno, M. S., Chow, C. Y., Jang, E. H., Debs, R. J., and Heath, T. D. (1995). A novel series of amphiphilic imidazolinium compounds for in vitro and in vivo gene delivery. Biochemistry 34, 13537-13544.

Sorlie, T., Perou, C. M., Tibshirani, R., Aas, T., Geisler, S., Johnsen, H., Hastie, T., Eisen, M. B., van de Rijn, M., Jeffrey, S. S., et al. (2001). Gene expression patterns of breast carcinomas distinguish tumor subclasses with clinical implications. Proc Natl Acad Sci USA 98, 10869-10874.

Sotiriou, C., Neo, S. Y., McShane, L. M., Korn, E. L., Long, P. M., Jazaeri, A., Martiat, P., Fox, S. B., Harris, A. L., and Liu, E. T. (2003). Breast cancer classification and prognosis based on gene expression profiles from a population-based study. Proc Natl Acad Sci USA 100, 10393-10398.

Yamashita, H., Yando, Y., Nishio, M., Zhang, Z., Hamaguchi, M., Mita, K., Kobayashi, S., Fujii, Y., and Iwase, H. (2006). Immunohistochemical evaluation of hormone receptor status for predicting response to endocrine therapy in metastatic breast cancer. Breast Cancer 13, 74-83.

The invention claimed is:

1. A method of treating breast cancer comprising administering a therapeutically effective amount of a combination of formulations to a human patient, wherein the formulations include
    (a) a formulation comprising a cationic liposomal preparation comprising at least one cationic lipid from about 30 mole % to about 99.9 mole %, a taxane in an amount of at least about 0.1 mole %, and at least one neutral lipid from about 30 mole % to about 70 mole %, wherein the liposomal preparation has a zeta potential in the range of about 0 mV to about 100 mV in about 0.05 mM KCl solution at about pH 7.5; and
    (b) a formulation comprising a non-liposomal preparation comprising a taxane; and wherein the formulation comprising the cationic liposomal preparation is administered in a single dose of between about 1 mg/m$^2$ and about 50 mg/m$^2$ of taxane and the formulation comprising the non-liposomal taxane is administered in a single dose of between about 20 mg/m$^2$ and about 100 mg/m$^2$ of taxane.

2. The method of claim 1, wherein the liposomal preparation has a zeta potential in the range of about 20 mV to about 100 mV in about 0.05 mM KCl solution at about pH 7.5.

3. The method of claim 1, wherein the taxane is paclitaxel or a derivative thereof.

4. The method of claim 3, wherein the cationic liposomal preparation comprises paclitaxel in an amount of at least about 2 mole % to about 8 mole % or at least about 2.5 mole % to about 3.5 mole %.

5. The method of claim 1, wherein the cationic lipid is selected from the group consisting of N-[1-(2,3-dioleyloxy) propyl]-N,N,N-trimethyl ammonium salt (DOTAP); dimethyldioctadecyl ammonium bromide (DDAB); 1,2-diacyloxy-3-trimethylammonium propane N-[1-(2,3-dioloyloxy) propyl]-N,N-dimethyl amine (DODAP); 1,2-diacyloxy-3-dimethylammonium propane; N-[1-(2,3-dioleyloxyl) propyl]-N,N,N-trimethylammonium chloride (DOTMA); 1,2-dialkyloxy-3-dimethylammonium propane; dioctadecylamidoglycylspermine (DOGS); 3β-[N—(N',N'-dimethylamino-ethane)carbamoyl]cholesterol (DC-Chol); 2,3-dioleyloxy-N-(2-(sperminecarboxamido)-ethyl)-N,N-dimethyl-1-propanaminium trifluoroacetate (DOSPA); β-alanyl cholesterol; cetyl trimethyl ammonium bromide (CTAB); diC14-amidine; N-tert-butyl-N'-tetradecyl-3-tetradecylamino-propionamidine; 14Dea2; N-(alpha-trimethylammonioacetyl)didodecyl-D-glutamate chloride (TMAG); O,O'-ditetradecanoyl-N-(trimethylammonioacetyl)diethanolamine chloride; 1,3-dioleoyloxy 2-(6-carboxy-spermyl)-propylamide (DOSPER); N,N,N',N'-tetramethyl-N,N'-bis(2-hydroxylethyl)-2,3-dioleoyloxy-1,4-butanediammonium iodide; 1-[2-(acyloxy)ethyl]2-alkyl (alkenyl)-3-(2-hydroxyethyl)-imidazolinium chloride; 1,2-dioleoyl-3-dimethyl-hydroxyethyl ammonium bromide (DORI); 1,2-dioleyloxypropyl-3-dimethyl-hydroxyethyl ammonium bromide (DORIE); 1,2-dioleyloxypropyl-3-dimethyl-hydroxypropyl ammonium bromide (DORIE-HP); 1,2-dioleyloxypropyl-3-dimethyl-hydroxybutyl ammonium bromide (DORIE-HB); 1,2-dioleyloxypropyl-3-dimethyl-hydroxypentyl ammonium bromide (DORIE-Hpe); 1,2-dimyristyloxypropyl-3-dimethyl-hydroxylethyl ammonium bromide (DMRIE); 1,2-dipalmityloxypropyl-3-dimethyl-hydroxyethyl ammonium bromide (DPRIE); 1,2-disteryloxypropyl-3-dimethyl-hydroxyethyl ammonium bromide (DSRIE); and 1,2-diacyl-sn-glycerol-3-ethylphosphocholine.

6. The method of claim 1, wherein the neutral lipid is selected from the group consisting of cholesterol; phospholipid; sphingolipid; and pegylated lipid with a neutral charge.

7. The method of claim 1, wherein the cationic liposomal preparation comprises DOTAP, DOPC, and paclitaxel.

8. The method of claim 7, wherein the cationic liposomal preparation comprises DOTAP, DOPC, and paclitaxel in a ratio of about 50:47:3.

9. The method of claim 1, wherein the formulations are administered sequentially.

10. The method of claim 1, wherein the formulations are administered simultaneously.

11. The method of claim 1, wherein the formulations are administered separately.

12. The method of claim 1, wherein the formulation comprising the cationic liposomal preparation and the formulation comprising the non-liposomal preparation are administered at different timepoints on the same day or on different days.

13. The method of claim 1, wherein the formulation comprising the cationic liposomal preparation is administered in a single dose of between about 20 mg/m$^2$ and about 50 mg/m$^2$ of taxane.

14. The method of claim 13, wherein the formulation comprising the cationic liposomal preparation is administered in a single dose of between about 20 mg/m$^2$ and about 40 mg/m$^2$ of taxane.

15. The method of claim 14, wherein the formulation comprising the cationic liposomal preparation is administered in a single dose of about 22 mg/m$^2$ of taxane.

16. The method of claim 1, wherein the formulation comprising the non-liposomal preparation is administered in a single dose of about 70 mg/m$^2$ of taxane.

17. The method of claim 15, wherein the formulation comprising the non-liposomal preparation is administered in a single dose of about 70 mg/m$^2$ of taxane.

18. The method of claim 1, wherein the formulation comprising the cationic liposomal preparation further comprises an anionic lipid in an amount of 30 mole % to 55 mole %.

19. The method of claim 5, wherein the 1-[2-(acyloxy) ethyl]2-alkyl (alkenyl)-3-(2-hydroxyethyl)-imidazolinium chloride is 1-[2-(9(Z)-octadecenoyloxy)ethyl]-2-(8(Z)-heptadecenyl-3-(2-hydroxyethyl)-imidazolinium chloride (DOTIM) or 1-[2-(hexadecanoyloxy)ethyl]-2-pentadecyl-3-(2-hydroxyethyl)imidazolinium chloride (DPTIM).

20. The method of claim 1, wherein the neutral lipid is selected from the group consisting of 1,2-diacyl-sn-glycero-3-phosphoethanolamine, 1,2-diacyl-sn-glycero-3-phosphocholine, and sphingomyelin.

21. The method of claim 20, wherein 1,2-diacyl-sn-glycero-3-phosphoethanolamine is 1,2-dioleoyl-sn-glycero-3-phosphoethanolamine (DOPE).

22. The method of claim 20, wherein 1,2-diacyl-sn-glycero-3-phosphocholine is 1,2-dioleoyl-sn-glycero-3-phosphocholine (DOPC).

23. The method of claim 6, wherein the phospholipid is a lysophospholipid.

* * * * *